United States Patent [19]
Schlicht et al.

[11] Patent Number: 5,628,800
[45] Date of Patent: May 13, 1997

[54] PROCESS FOR THE PREPARATION OF WATER-DISPERSIBLE GRANULES

[75] Inventors: Rainer Schlicht, Bad Camberg; Hans Röchling, Bad Soden am Taunus; Konrad Albrecht, Kelkheim/Taunus, all of Germany

[73] Assignee: Hoechst Aktiengesellschaft, Frankfurt, Germany

[21] Appl. No.: 496,273

[22] Filed: Mar. 20, 1990

[30] Foreign Application Priority Data

Mar. 22, 1989 [DE] Germany .................. 39 09 455.3

[51] Int. Cl.$^6$ .................. C22B 1/14; A01N 25/00
[52] U.S. Cl. .................. 23/313 FB; 424/405
[58] Field of Search .................. 23/313 FB; 8/490; 71/92; 424/405

[56] References Cited

U.S. PATENT DOCUMENTS

| | | | |
|---|---|---|---|
| 2,689,973 | 9/1954 | Lee et al. | 23/313 FB |
| 3,748,103 | 7/1973 | Bean et al. | 23/313 FB |
| 3,849,233 | 11/1974 | Lykov et al. | 23/313 FB |
| 3,920,442 | 11/1975 | Albert et al. | 71/92 |
| 4,134,725 | 1/1979 | Büchel et al. | 8/490 |
| 4,619,843 | 10/1986 | Mutsers | 427/213 |
| 4,701,353 | 10/1987 | Mutsers et al. | 427/213 |
| 4,936,901 | 6/1990 | Surgant, Sr. et al. | 71/92 |
| 4,968,500 | 11/1990 | Bertsch-Frank et al. | 23/313 FB |

FOREIGN PATENT DOCUMENTS

| | | |
|---|---|---|
| 0026918 | 4/1981 | European Pat. Off. . |
| 0141437 | 5/1985 | European Pat. Off. . |
| 0141436 | 5/1985 | European Pat. Off. . |
| 1401304 | 7/1975 | United Kingdom . |
| 2063759 | 6/1981 | United Kingdom . |

OTHER PUBLICATIONS

H.B. Ries, Hardheim, Granuliertechnik und Granuliergeräte Aufbereitungstechnik, Nr. 3, (1970) No month 1.–4. Leil, S. 147 ff (Minimals—no translation).
D. Jones et al., Introduction to Fluid Bed Granulation Glatt GmbH in D–7851 Binzen/Lörrach No Date.
M. Rosch et al., Verfahrenstechnik, vol. 9, Nr. 2, (1975), S. 59 ff. Minimal—no translation.

*Primary Examiner*—Ferris Lander
*Attorney, Agent, or Firm*—Curtis, Morris & Safford, P.C.

[57] ABSTRACT

Granules can be prepared from powders of active compounds by the counter-current principle by fluidization in a stream of air and spraying of a solution of adhesive. Dispersions or solutions of active compounds can be granulated in accordance with the invention if the aqueous dispersion or solution is sprayed by the counter-current principle into the gas stream of a fluidizing chamber and is caused to fluidize, the formation of granules being started, in a start-up phase, at 10 to 60% of the maximum gas flow and at only up to 30% of the maximum feed rate of dispersion or solution, and subsequently the feed rate and the gas flow are increased up to the maximum values for the feed rate and the gas flow, and, in the main phase, the formation of granules is continued at maximum gas flow and maximum feed rate.

Granules prepared in this way, containing pesticides as the active compounds, can be used as plant protection agents or pest control agents.

19 Claims, 1 Drawing Sheet

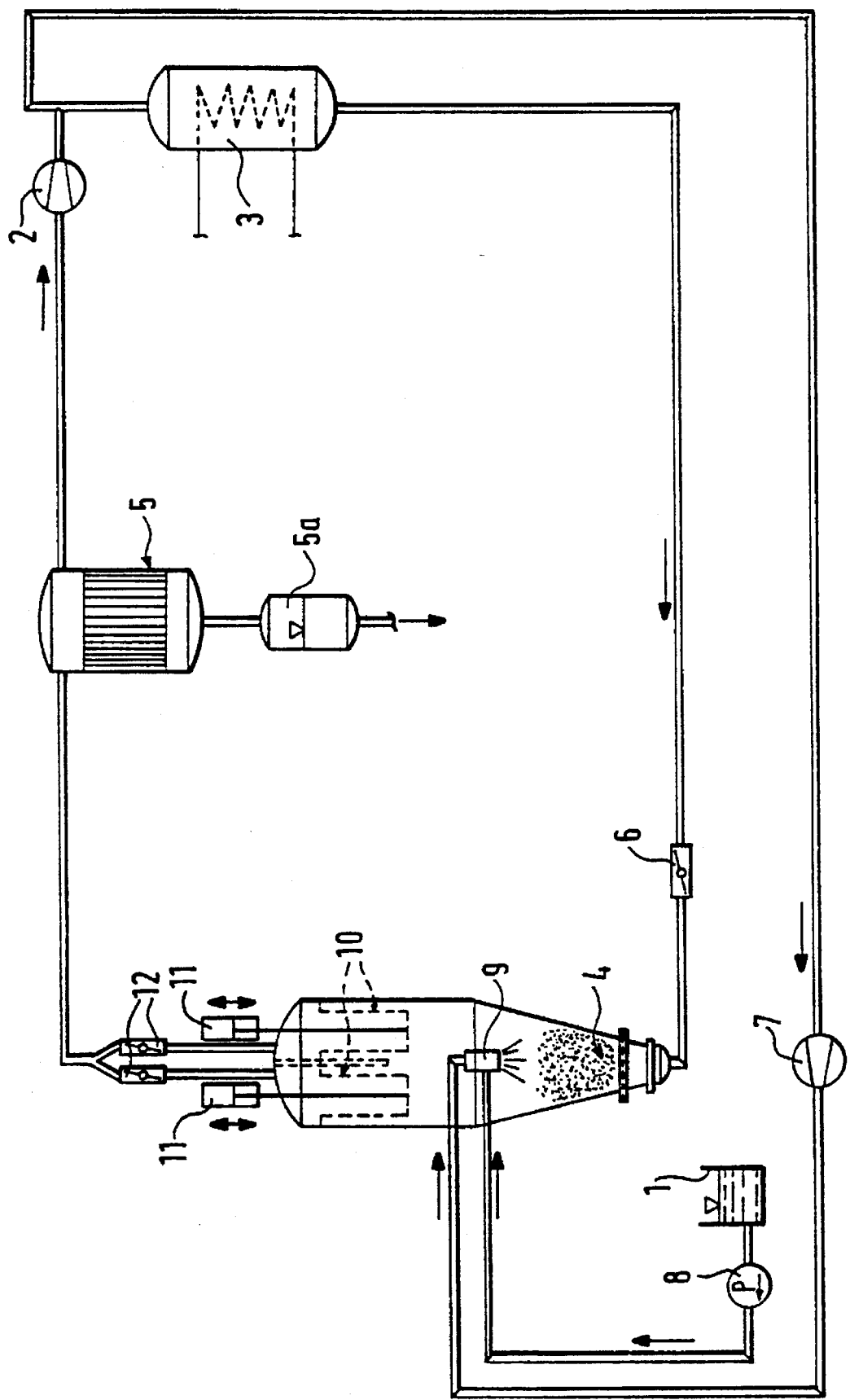

PROCESS FOR THE PREPARATION OF WATER-DISPERSIBLE GRANULES

DESCRIPTION

The present invention relates to a process for the preparation of water-dispersible granules which are preferably used in plant protection.

Plant protection agents are marketed mainly in the form of wettable powders, emulsifiable concentrates or aqueous dispersions. Spray liquors are prepared by stirring the agents into water.

Handling these preparation forms is not without problems. Thus the preparation and use of wettable powder formulations often result in nuisance caused by dust.

Emulsifiable concentrates contain solvents which can be readily flammable, can irritate the skin or can cause an odor nuisance.

When stored for long periods, dispersions can form sediments which are hard to shake up. In addition, there are often problems concerned with the disposal of the packaging materials in this type of formulation.

Water-dispersible granules (known as "WDG" for short) do not have these disadvantages, since they are free-flowing, of low dust content and readily meterable. They can be packed without problems in polyethylene containers, gussetted bags made of laminated film (paper/aluminum/plastic) or cardboard drums, which can be disposed of easily.

Numerous processes are available for the industrial production of dispersible granules (cf. H. B. Ries "Granuliertechnik und Granuliergeräte" ("Granulation Technology and Granulation Equipment") in Aufbereitungstechnik No. 3, 1970, page 147 and M. Rosch and R. Probst in Verfahrenstechnik 9 (1975), pages 59 to 64). In particular, it is known to prepare water-dispersible granules by the fluidized bed process, which can be operated counter-current or co-current.

Patent Specifications U.S. Pat. No. 3,920,442 and GB-A 1,401,304 and also M. Rosch and R. Probst in Verfahrenstechnik 9 (1975) page 59 describe the counter-current process in which the powder of active compound, essentialy finely ground and mixed with inert material and formulation auxiliaries, is fluidized by an air stream entering from below and is agglomerated by means of an adhesive solution sprayed on from above.

In the co-current process, as described in EP-A 0,026,918, EP-A 0,141,436 and EP-A 0,141,437 and in Verfahrenstechnik 9 (1975), pages 61/62, a solution, melt or dispersion of product is sprayed into the product vessel of the granulating apparatus in co-current with the air which is fluidizing the solid.

In order to ensure satisfactory use, water-dispersible granules must be readily wetted when introduced into water, must disintegrate as spontaneously as possible and must form a suspension of good suspension properties. In the case of granules produced by the fluidized bed process the wettability and the suspension properties are determined by parameters of process engineering and by the formulation agents used.

Thus granule-grains which are readily dispersible and also have an adequate mechanical strength are obtained by the counter-current process by fluidized bed granulation if the formulation recipe is suitable.

On the other hand, the use of a dispersion of active compound, which is usually employed in the co-current process, as the starting material for granules is cheaper than the use of a powdered active compound, since wet grinding is easier to carry out in industry than dry grinding.

Dispersions of active compounds have hitherto not been used for the preparation of water-dispersible granules by the fluidized bed counter-current process which is favorable for the properties of the granules. Commercial fluidized bed granulation plants, such as, for example, those of the firms Glatt and Aeromatik operate on the counter-current process and are intended for the granulation of finely ground powder mixtures; the desired granules are obtained by spraying a solution of adhesive into the powder which has been fluidized with hot air. The equipment is operated by the batch process (M. Rosch and R. Probst in Verfahrenstechnik 9 (1975), page 59 or D. Jones, Introduction to Fluid Bed Granulating, Glatt GmbH, D-7851 Binzen/Lörrach).

If granules are to be prepared from dispersions of active compounds in the plants described, a powder of the same composition as the dry substance in the dispersion to be granulated is required at the start of the process as an initial charge.

A powder of this type can be obtained either by drying the dispersion in a spray tower or by mixing the active compound with the formulating agents and then carrying out dry grinding. Both measures are involved and expensive, since they require additional equipment.

It has now been found that, surprisingly, dispersions of active compounds can be granulated without further treatment in counter-current granulation plants without first having to be converted into a fine powder by drying and grinding, if the granulation process is carried out at the start by a start-up procedure defined by certain parameters. The process can, inter alia, be carried out by means of the counter-current granulating plants which can be used as above for the granulation of powders.

The invention relates to a process for the preparation of water-dispersible granules from aqueous dispersions or solutions of solids, also containing, if appropriate, formulation auxiliaries, which comprises spraying the aqueous dispersion or solution by the counter-current principle into the gas stream of a fluidizing chamber and causing it to fluidize, starting the formation of granules in a start-up phase at 10 to 60% of the maximum gas flow and at only up to 30% of the maximum feed rate of dispersion or solution, and subsequently increasing the feed rate and the gas flow up to the maximum values for the feed rate and the gas flow, and, in the main phase, continuing the formation of granules at maximum gas flow and maximum feed rate.

In particular, it is advantageous to start the granulation process with an empty fluidizing chamber (ie. without an initial charge of the aqueous dispersion or. solution), at 40 to 50% of the maximum gas flow and at 5 to 15% of the maximum feed rate of the dispersion or solution.

Suitable gases are those which are inert under the conditions of the process.

The gas inlet temperature is kept roughly constant, preferably at a desired value, during the whole process. The gas inlet temperature is preferably in the range from 90° C. to 180° C., in particular 120° to 150° C.

The optimum mode of operation in the start-up phase in respect of the level and temperature of the gas stream, temperature of the granules and feed rate of the dispersion can be determined easily in an individual case, for example by using a factorial design of tests.

Counter-current plants suitable for the process according to the invention are those which are otherwise intended for the preparation of granules from pulverulent solids. The customary plants for powder granulation as a rule contain a fluidizing chamber into which a stream of gas (in most cases dry, heated air, nitrogen, carbon dioxide or mixtures thereof) enters through a perforated plate, and adhesive solution is sprayed via a nozzle from above (against the gas stream) onto the powder previously placed in the fluidizing chamber. In the case according to the invention, however, no powder is previously placed, but the dispersion or solution of the solid to be granulated is sprayed into the fluidizing chamber via the nozzle mentioned, instead of a solution of an adhesive. The nozzles used in accordance with the invention can be very varied, preferably single-fluid or two-fluid nozzles.

As a rule, the granulating plants also contain a main filter which is mounted above the nozzle mentioned and traps the finely particulate granules or dusts carried over by the gas stream. The main filter preferably consists of two parallel filters which are vibrated alternately in a short sequence so that trapped finely particulate granules and dusts fall back into the fluidizing chamber again.

For carrying out the process according to the invention by means of the granulating plants, the feed rate in the start-up phase should be adjusted to suit the drying properties of the granules. In a preferred procedure the feed rate in the start-up phase is increased substantially simultaneously with the gas flow at such a rate that the temperature t of the granules formed remains in the range from $(t_m+20°\ C.)$ to $(t_m-20°\ C.)$, in particular $(t_m+5°\ C.)$ to $(t_m-5°\ C.)$, $t_m$ being the average value of the temperature in $°\ C.$ For example, the feed rate of the dispersion in the start-up phase can be increased in steps or continuously, the maximum feed rate being reached preferably after 10 to 50 minutes, especially 20 to 35 minutes. In the case of stepwise metering the feed rate is increased, for example, in a 0.1 to 4 minute cycle, by 1 to 5% of the maximum feed rate. The optimum increase in the feed rate in an individual case depends on the formulation and the drying properties of the granules.

The desired product temperature is preferably maintained substantially constant by simultaneous increase in the gas flow. When the maximum gas flow has been reached, it is then also maintained approximately constant, and the product temperature up to the maximum filling of the chamber is controlled by the metering of the dispersion. When spraying in is complete, the vibration of the main filter is switched off and the granules obtained are, as a rule, subsequently dried by maintaining the gas flow with the feed of dispersion or solution stopped.

When the product has been drawn off, the dust collected in the main filter is removed by vibration and is thus available for the next batch. The amount of this dust depends on the formulation and can be utilized in the following batch to accelerate the rate of increase and thus to shorten the start-up program.

The process described here can advantageously be used for granulating dispersions and solutions of active compounds. The dispersions or solutions advantageously have a solids content of 20 to 70% by weight, in particular 35 to 60% by weight.

The process described can be employed to granulate those materials from which an aqueous dispersion or an aqueous solution can be prepared. These are preferably solids which are dispersible in water, if appropriate in the presence of suitable dispersing agents.

If a dispersion is used, the customary limitation under which it is only possible to grind materials having a melting point higher than 70° .C does not apply, since in the present case the dispersion is only employed in the form of an intermediate product and can therefore be cooled during preparation and storage.

Examples of materials which have the required physicochemical properties and can be formulated as water-dispersible granules in the process described herein are solids belonging to the group comprising organic and inorganic plant protection agents and pest control agents, pigments, feedstuffs inter alia.

The process is of particular interest for preparing granules using active compounds belonging to the group comprising pesticides, in particular herbicides, insecticides or fungicides. Examples of suitable active compounds are herbicidal urea derivatives, such as, for example, linuron, monolinuron, isoproturon or diuron, or substituted phenoxypropionic acid esters, such as, for example, fenoxaprop-ethyl or diclofop-methyl, total herbicides, such as glufosinates-ammoniumor glyphosates, or insecticides belonging to the group comprising pyrethroids, such as, for example, deltamethrin, or chlorinated bicyclic compounds, such as endosulfan, or fungicides belonging to the group comprising triphenyltin compounds, such as, for example, fentinhydroxide or fentin acetate, or benzimidazole derivatives, such as carbendazim, or dithiocarbamates, such as maneb or mancozeb, and also combinations of the triphenyltin compounds or the benzimidazole derivatives with the dithiocarbamates. These compounds and a number of analogs are described in Ch. R. Worthing, S. B. Walker "The Pesticide Manual, British Crop Protection Council".

The dispersion or solution of the solid to be granulated in most cases also contains other solid or liquid substances as auxiliaries which are either indispensable for the technical properties relating to the use of the materials or active compounds and/or promote the formation of granules. For example, the dispersions or solutions of the pesticides can contain customary formulation auxiliaries which are required for the technical properties relating to the use of the pesticides and the optimum biological action thereof and the water-dispersible granules, such as, for example, wetting and dispersing agents, penetration promoters, adhesives, tackifiers, stabilizers and so on.

Examples of suitable wetting and dispersing agents are anionic or cationic, amphoteric and nonionic surface-active substances, in particular customary anionic dispersing agents, such as the Na salt of the sulfonic acid formed from m-cresol+formaldehyde+Na sulfite (dispersing agent 1494®), sodium oleoylmethyltauride (®Arkopon T), sodium methoxyligninsulfonate (®Vanisperse CB), sodium ligninsulfonate (®Borresperse 3 A), sodium methylnaphthalenesulfonate (®Supragil MNS 90), the sodium salt of 3-nucleus-nonylphenolnovolak-18EO-sulfosuccinic acid half-ester (dispersing agent 1728®, 18EO=ethoxylated with 18 moles/mole of ethylene oxide) and the sodium salt of isodecylsulfosuccinic acid half-ester.

The sodium salt of a dinaphthylmethanedisulfonic acid (®Dispersogen A, ®Tamol NNO), the sodium salt of a sulfonic acid formed from cresol+formaldehyde+Na sulfite+hydroxynaphthalenesulfonic acid (dispersing agent SS®), the sodiumsalt of dibutylnaphthalenesulfonic acid, sodium polycarboxylate (®Sopropon T 36), potassium polycarboxylate (®Dispersant DG), sodium phenylsulfonate (®Dispersant GN), sodium alkylnaphthalenesulfonate (®Supragil WP), sodium naphthalenesulfonate, condensed, (®Supragil NS 90), the Na or K salt of a carboxylated copolymer in combination with an anionic dispersing agent (®Geropon Sc 211 or 213, RhOne Poulenc) and calcium or sodium ligninsulfonates of very different origins.

The dispersions or solutions can also contain adhesives, such as, for example, starch syrup, dextrose, various types of cellulose, for example methylcellulose or carboxymethylcellulose (for example ®Tylose brands), polyethylene glycol brands, partially saponified polyvinyl acetate (®Mowiol grades, for example 3/83) and polyvinylpyrrolidone (®Luviskol grades, for example ®Luviskol E 30).

In addition the granules can contain inert materials, such as $SiO_z$, chalk, starch and kaolinite, binders, such as polyvinylpyrrolidone, saccharides and polyvinyl alcohol, anti-foaming agents, such as trialkyl phosphates, or agents which promote the bursting of the granule-grains in water, such as pentasodium triphosphate.

The contents of active compound in the granules according to the invention are 1 to 95% by weight, in particular 40 to 90% by weight.

EXAMPLES

A) General description of the process (see the attached figure)

The dispersion or solution to be spray-dried is initially placed in a receiver (1). The plant is then blanketed with nitrogen. The dry gas circulation is then set in motion by means of the fan (2). In the course of this the dry gas is heated to the desired temperature in the heater (3) and, after flowing through the fluidizing chamber (4) is cooled to a desired temperature in the condenser (5). Both temperatures are constant during the whole process. The amount of the gas used in the circulation system can be adjusted via a gas flap-valve (6). When the temperature in the empty fluidizing chamber has reached the desired level, the nozzle (9) (two-fluid nozzle) is set in operation by switching on the compressor (7) and the pump (8). The nozzle receives a stream of nitrogen which assists the spray-drying of the dispersion or solution and which is adjusted to suit the flow of dry gas. A small amount of liquid is used at the start and this is increased steadily in accordance with a specific start-up program. The amount of dry gas is increased in such a way that the product temperature is kept constant at a desired level. The main filter (10) consists of two or more sub-filters through which the gas stream is caused to flow or not to flow alternately in a short sequence by opening and closing the corresponding cut-off valves (12), and which are vibrated by means of the operating gear (11), in each case with the gas flow interrupted, so that the dust formed falls back into the fluidizing chamber again.

When the maximum amount of dry gas has been reached, the process changes into a constant main program in which operations are carried out at the desired product temperature at the highest possible output. The water from the dispersion or solution is discharged by means of the condenser (5) via the condensate receiver (5a) and can then be employed for making up new solution or dispersion and thus re-used in the process. When the maximum filling of the fluidizing chamber has been reached, the pump, the compressor and the vibration are switched off. This is followed by a brief after-drying and air-classifying phase. The fan and the other units are then switched off. When the granules have been drawn off, a new granulation process can be started in the manner described. As a rule, the plant also contains connections and regulators for the supply and removal of nitrogen and also pressure regulators.

In addition the plant can also contain further filters for trapping very fine dusts.

B) Test methods

An assessment scale from 1 to 4 has been taken as a basis for estimating the spontaneous dispersibility of the granule formulation in water:

1 g of the granules is put into a 1-liter measuring cylinder filled with standardized water (30° C., 342 ppm of water hardness). After 1 minute the measuring cylinder is turned slowly through 180° and is brought back again into the initial position. This procedure is repeated three times.

Assessment scale:

1=all the grains of the granules have been dispersed.

If undispersed granule-grains are present after the first test, the mixture is again shaken 3 times as described 2 minutes after the start of the test, and the result is assessed as follows:

2=the granules are now completely dispersed.

3=residues of the granules are not dispersed.

4=the granules are predominantly not dispersed.

The suspending property was indicated as the amount of the preparation (% by weight) which is present in the upper nine tenths by volume of a suspension after the expiry of a sedimentation time of 30 minutes (see CIPAC Handbook volume 1 (1970), page 861).

The amount of substance which remains on a sieve of 250 μm or 71 μm after rinsing for 10 minutes with a definite amount of water is designated the wet sieve residue. A description of the method is given in "Specification for pesticides used in public health", WHO Geneva, page 281 (1973).

C) Illustrative embodiments

In the following examples, percentages are percentages by weight unless otherwise stated.

Example 1

Preparation of water-dispersible granules with isoproturon 30.5 kg of a 42.4% strength aqueous dispersion of N-(4-isopropylphenyl)-N'N'-dimethylurea (isoproturon) and customary formulation auxiliaries having a total solids content of 53% are initially placed in the fluidized bed granulating plant described under A), and initially all the constant parameters were set as follows:

Dry gas temperature: 150° C.

Condenser temperature: 33° C.

After the temperature in the fluidizing chamber had reached 50° C., the process was started at a dry gas rate of 250 m³/hour and a dispersion feed of 50 g/minute. The feed rate of dispersion via the nozzle (9) (see figure) was increased by 25 g/minute after every minute during the start-up phase. The flow of dry nitrogen controlled by the gas flap-valve was increased simultaneously, so that the product temperature remained constant at 50° C.

Granulation was finished at a maximum gas flow of 600 m³/hour and a feed rate of 710 g/minute.

Subsequent to the after-drying and air classification, the granules were removed from the fluidizing chamber.

| Yield: | 16 kg of granules containing 80.5% of active substance |
|---|---|
| Average particle size: | 0.73 mm |
| Spontaneous dispersibility: | 1 |
| Wet sieve residues: | on 0.25 mm < 0.01%; on 0.071 mm < 0.1% |
| Suspending property: | 99% |
| Moisture content: | 0.5% |

Example 2

Preparation of water-dispersible granules with triphenyltin hydroxide (TPTH) 28 kg of a 43% aqueous dispersion of TPTH having a solids content of 53.7% were initially placed in the fluidized bed granulating plant described under A). Initially all the constant parameters were set as follows:

Dry gas temperature: 120° C.

Condenser temperature: 33° C.

When the temperature in the fluidizing chamber had reached 55° C., granule-formation was started analogously to Example 1 at a dry gas flow of 200 m³/hour and a feed rate of 25 g/minute of dispersion.

After every 1.5 minutes the feed rate was increased by 25 g/minute. The dry gas rate was increased simultaneously at such a rate that the temperature of the granules formed (product temperature) remained virtually constant at 50° C.

Granulation was finished at a dry gas flow of 600 m³/hour and a feed rate of 400 g/minute.

Subsequent to after-drying and air classification, the granules were drawn off from the fluidizing chamber (4).

| Yield: | 15 kg of granules containing 80.3% of active substance |
|---|---|
| Average particle size: | 0.410 mm |
| Spontaneous dispersibility: | 1 |
| Wet sieve residues: | on 0.25 mm < 0.01%; on 0.071 mm < 0.1% |
| Suspending property: | 88% |
| Moisture content: | 0.7% |

Example 3

Preparation of water-dispersible granules with glufosinate-ammonium 34.5 kg of a 7.6% strength aqueous solution of glufosinate-ammonium and auxiliaries having a solids content of 38% were initially placed in the fluidized bed granulating plant described above. Initially the parameters were set as follows:

Dry gas temperature: 150° C.

Condenser temperature: 33° C.

When the temperature in the fluidizing chamber had reached 95° C., granule-formation was started at a dry gas flow of 350 m³/hour and a feed rate of 25 g per minute of active compound solution.

The feed rate was increased by 25 g/minute after every 4 minutes. The dry gas flow was increased simultaneously at such a rate that the product temperature could be maintained virtually constant at about 90° C.

Granulation was terminated at a dry gas flow of 600 m³/hour and a feed rate of 280 g/minute.

Subsequent to after-drying and air classification, the granules were drawn off.

| Yield: | 13 kg of granules containing 20.7% of active substance |
|---|---|
| Average particle size: | 1.1 mm |
| Spontaneous dispersibility: | 2 |
| Wet sieve residues: | on 0.25 mm < 0.01%; on 0.071 mm < 0.1% |
| Suspending property: | clear solution |
| Moisture content: | 1.5% |

We claim:

1. A process for the preparation of water-dispersible granules from an aqueous dispersion or solution of solids, which comprises spraying the aqueous dispersion or solution by the counter-current principle into the gas stream of a fluidizing chamber and causing it to fluidize, starting the formation of granules in a start-up phase at 10 to 60% of the maximum gas flow and at only up to 30% of the maximum feed rate of dispersion or solution, and subsequently increasing the feed rate and the gas flow up to the maximum values for the feed rate and the gas flow, and, in the main phase, continuing the formation of granules at maximum gas flow and maximum feed rate.

2. The process as claimed in claim 1, wherein the formation of granules is begun in the start-up phase at 40 to 50% of the maximum gas flow and at 5 to 15% of the maximum feed rate of dispersion or solution.

3. The process as claimed in claim 1, wherein the gas stream at the entry into the fluidizing chamber has a temperature in the range from 90° to 180° C.

4. The process as claimed in claim 3, wherein the temperature is within the range from 120° to 150° C.

5. The process as claimed in claim 1, wherein the gas stream before entry into the fluidizing chamber has a constant temperature during the process.

6. The process as claimed in claim 1, wherein the feed rate in the start-up phase is increased substantially simultaneously with the gas flow at such a rate that the temperature t of the granules formed is in the range from $(t_m+20°$ C.) to $(t_m-20°$ C.), $t_m$ being the average value of the temperature in ° C.

7. The process as claimed in claim 1, wherein the feed rate in the start-up phase is increased, in a 0.1 minute to 4 minute cycle, by 1 to 5% of the maximum feed rate, per cycle.

8. The process as claimed in claim 1, wherein the feed rate in the start-up phase is increased continuously.

9. The process as claimed in claim 1, wherein fine granules and dusts carried over by the gas stream are trapped by a filter placed downstream, and the filter is shaken continuously and the trapped granules and dusts fall back into the fluidizing chamber.

10. The process as claimed in claim 1, wherein nitrogen or air is used as the gas for the gas stream.

11. The process as claimed in claim 1, wherein the solids dispersed or dissolved in the dispersion or solution, respectively, contain active compounds selected from the group consisting of pesticides.

12. The process as claimed in claim 1, wherein the dispersion or solution contain one or more adhesives, tackifiers, wetting and dispersing agents and stabilizers for the formation of granules.

13. The process as claimed in claim 11, wherein the dispersion or solution contain one or more adhesives, tackifiers, wetting and dispersing agents and stabilizers for the formation of granules.

14. The process as claimed in claim 11, wherein the dispersion or solution contains auxiliaries for the formulation of pesticides.

15. The process as claimed in claim 1 wherein the dispersion or solution also contains formulation auxiliaries.

16. The process as claimed in claim 1, wherein the feed rate in the start-up phase is increased continuously.

17. The process as claimed in claim 1, wherein fine granules and dusts carried over by the gas stream are trapped by a filter placed downstream, and the filter is shaken continuously and the trapped granules and dusts are conveyed thither.

18. The process as claimed in claim 1, wherein fine granules and dusts carried over by the gas stream are trapped by a filter placed downstream, and the filter is shaken at intervals of time during the process and the trapped granules and dusts fall back into the fluidizing chamber.

19. The process as claimed in claim 1, wherein fine granules and dusts carried over by the gas stream are trapped by a filter placed downstream, and the filter is shaken at intervals of time during the process and the trapped granules and dusts are conveyed thither.

* * * * *